(12) United States Patent
Wang

(10) Patent No.: US 9,528,938 B2
(45) Date of Patent: Dec. 27, 2016

(54) FLUORESCENCE BIOPSY SPECIMEN IMAGER AND METHODS

(71) Applicant: LI-COR, Inc., Lincoln, NE (US)

(72) Inventor: Han-Wei Wang, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 15/049,970

(22) Filed: Feb. 22, 2016

(65) Prior Publication Data

US 2016/0245753 A1    Aug. 25, 2016

Related U.S. Application Data

(60) Provisional application No. 62/185,407, filed on Jun. 26, 2015, provisional application No. 62/119,660, filed on Feb. 23, 2015.

(51) Int. Cl.
*G01N 21/64* (2006.01)
*H04N 7/18* (2006.01)
(Continued)

(52) U.S. Cl.
CPC ......... *G01N 21/6456* (2013.01); *G06T 7/0012* (2013.01); *G06T 17/20* (2013.01);
(Continued)

(58) Field of Classification Search
CPC ............ G01N 21/6456; G01N 2201/12; G01N 2201/06113; H04N 7/181; H04N 5/2256; G06T 17/20; G06T 7/0012; G06T 2207/30096; G02B 21/26
See application file for complete search history.

(56) References Cited

U.S. PATENT DOCUMENTS 5,103,338 A    4/1992  Crowley et al.
5,812,265 A    9/1998  Hoshiyama
(Continued)

FOREIGN PATENT DOCUMENTS

DE    10 2011 104 216 A1    12/2012
WO        2007/030424 A2     3/2007
(Continued)

OTHER PUBLICATIONS

International Application No. PCT/US2016/018972, International Search Report and Written Opinion mailed on Jun. 23, 2016, 10 pages.
(Continued)

*Primary Examiner* — Neil Mikeska
(74) *Attorney, Agent, or Firm* — Kilpatrick Townsend and Stockton LLP

(57) ABSTRACT

Biopsy imaging devices with an imaging stage configured to rotate and tilt a biological sample, as well as a method for using it, are described. The stage can use rotating bearings or extendible, telescoping arms. The device has a white light for taking normal pictures and a near-infrared laser light for causing a fluorescence-biomolecule probed sample to fluoresce for fluorescence images in a light-tight housing. A set of both types of pictures are taken from angles around, above, and below the biopsy sample with one or more cameras to generate a 3-D model in a computer of the biopsy with fluorescence markings. The 3-D model can then be rendered and viewed on a display by a surgeon to determine if sufficient margins were removed from the patient.

17 Claims, 12 Drawing Sheets

(51) Int. Cl.
*G06T 17/20* (2006.01)
*G06T 7/00* (2006.01)
*H04N 5/225* (2006.01)

(52) U.S. Cl.
CPC ........... *H04N 5/2256* (2013.01); *H04N 7/181* (2013.01); *G01N 2201/06113* (2013.01); *G01N 2201/12* (2013.01); *G06T 2207/30096* (2013.01)

(56) References Cited

U.S. PATENT DOCUMENTS

| | | | |
|---|---|---|---|
| 6,356,272 | B1 | 3/2002 | Matsumoto et al. |
| 6,711,433 | B1 | 3/2004 | Geiger et al. |
| 7,218,393 | B2 | 5/2007 | Sharpe et al. |
| 7,286,232 | B2 | 10/2007 | Bouzid |
| 7,453,456 | B2 | 11/2008 | Petrov et al. |
| 7,505,124 | B2 * | 3/2009 | Kreckel ............. G01N 21/8806 356/237.1 |
| 7,715,523 | B2 | 5/2010 | Lafferty |
| 7,929,743 | B2 | 4/2011 | Khorasani |
| 8,220,415 | B2 | 7/2012 | Ragatz et al. |
| 8,503,602 | B2 | 8/2013 | Lafferty |
| 8,741,232 | B2 | 6/2014 | Baysal et al. |
| 8,754,384 | B1 | 6/2014 | Persoon et al. |
| 8,851,017 | B2 | 10/2014 | Ragatz et al. |
| 9,053,563 | B2 | 6/2015 | Embrey |
| 2004/0101088 | A1 | 5/2004 | Sabol et al. |
| 2005/0046840 | A1 | 3/2005 | Kusuzawa |
| 2005/0227374 | A1 | 10/2005 | Cunningham |
| 2008/0077019 | A1 | 3/2008 | Xiao et al. |
| 2009/0011386 | A1 * | 1/2009 | Eiff ........................ G01B 11/24 433/215 |
| 2009/0032731 | A1 | 2/2009 | Kimura et al. |
| 2009/0129543 | A1 * | 5/2009 | Le Gros ................... G21K 7/00 378/62 |
| 2009/0208072 | A1 | 8/2009 | Seibel et al. |
| 2009/0234225 | A1 | 9/2009 | Martin et al. |
| 2011/0116694 | A1 | 5/2011 | Gareau |
| 2012/0194663 | A1 | 8/2012 | Haisch et al. |
| 2014/0125790 | A1 | 5/2014 | Mackie et al. |
| 2014/0163388 | A1 | 6/2014 | Sasayama et al. |
| 2014/0276008 | A1 | 9/2014 | Steinbach et al. |
| 2015/0022824 | A1 | 1/2015 | Babayoff |
| 2015/0105283 | A1 | 4/2015 | Weiss et al. |

FOREIGN PATENT DOCUMENTS

| | | |
|---|---|---|
| WO | 2009/115061 A1 | 9/2009 |
| WO | 2016/100214 A1 | 6/2016 |

OTHER PUBLICATIONS

"Arctec Eva Fast Handheld 3D Scanner for Professionals," http://www.artec3d.com/hardware/artec-evat/, retrieved Apr. 19, 2016, 6 pages.
"BioVision Digital Specimen Radiography (DSR) System," (Bioptics, Inc.), Premarket Notification 510(k) Summary, May 2009, 5 pages.
Fang et al., "Combined Optical and X-ray Tomosynthesis Breast Imaging," Radiology, Jan. 2011, vol. 258, No. 1, pp. 89-97.
Faxitron —"BioVision Surgical Specimen Radiography System," Faxitron Bioptics LLC, http://www.faxitron.com/medical/products/biovision.html, Retrieved Apr. 18, 2016, 2 pages.
Faxitron —"Path Vision," Faxitron Bioptics LLC, http://www.faxitron.com/medical/products/pathvision.html, Retrieved Apr. 18, 2016, 2 pages.
"Optical Scatter Imaging System for Surgical Specimen Margin Assessment During Breast Conserving Surgery," Project Information, U.S. Department of Health & Human Services, NIH Research Portfolio Online Reporting Tools, Updated Apr. 18, 2016, Project No. 1RO1CA192803-01, https://projectreporternih.gov/project_info_description.cfm?aid=8840807&icde=28280616& . . . , 2 pages.
PerkinElmer, "Every Cancer Tells a Story If You Have the Tools to Read It," Solutions for Cancer Research, AACR Annual Meeting, Apr. 18-22, 2015, http://go.perkinelmer.com/webmail/32222/179460051/9c4865b118d5295e96e973a5b6c28bad, 2 pages.
PerkinElmer, "Every Cancer Tells a Story If You Have the Tools to Read It," http://go.perkinelmer.com/1/32222/2015-03-26/3rww9?utm_content=LST-AACR-GLO-Q . . . Retrieved Apr. 15, 2015, 2 pages.
TomoWave Laboratories "Imaging Modules," http://www.tomowave.com/imaging-modules.html, Retrieved Apr. 18, 2016, 1 page.
Wu et al. "Rotational imaging optical coherence tomography for full-body mouse embryonic imaging," *Journal of Biomedical Optics*, Feb. 2016, vol. 21(2), pp. 026002-1-026002-9.
International Application No. PCT/US2016/039382, International Search Report and Written Opinion mailed on Sep. 13, 2016, 14 pages.

* cited by examiner

FLUORESCENCE BIOPSY SPECIMEN IMAGER AND METHODS

CROSS-REFERENCES TO RELATED APPLICATIONS

This application claims the benefit of U.S. Provisional Application No. 62/185,407, filed Jun. 26, 2015, and U.S. Provisional Application No. 62/119,660, filed Feb. 23, 2015, which are hereby incorporated by reference in their entireties for all purposes.

STATEMENT AS TO RIGHTS TO INVENTIONS MADE UNDER FEDERALLY SPONSORED RESEARCH AND DEVELOPMENT

Not Applicable

BACKGROUND

The main goal of cancer surgery is to excise tumors en bloc with adequate tumor free margins so that morbidity and reoccurrence is minimized. While surgery remains an effective therapy for solid tumors, about one-third of patients who undergo surgery develop local recurrences. As surgeons rely on surgical pathology to determine the extent of the excision needed to eradicate a tumor, complete accuracy and efficacy of surgery has yet to be achieved. Surgical pathology routinely uses frozen sectioning to prepare surgically removed tissue into approximately 10 μm thick slides, and follow-up with histological examination using hematoxylin and eosin (H&E) staining. This allows the determination of the presence of disease in the surgical margins.

Notably, gross examination can be an important procedure in a 'frozen section room' because it locates disease tissues to be histologically sectioned and analyzed. Because only a small fraction of the specimen will be histologically examined due to time and personnel constraints, a way to improve gross examination is the best defense against sampling errors. These errors negatively impact the ability of the pathologist to provide accurate diagnosis and ultimately affect the ability of the surgeon to achieve clear margin status.

In view of the foregoing, new systems, devices and methods are needed to improve gross examination and margin status. The present invention satisfies these and other needs.

BRIEF SUMMARY

Generally, imaging systems and methods of use are described that hold a biological sample, such as a tumor surgically removed from a patient, in front of a camera system. The camera system takes two-dimensional (2-D) pictures at many different angles, above, to the side, and from underneath the sample by either moving the sample around, moving the camera system around the sample, or a combination thereof. In order to acquire pictures from underneath the sample, the sample can be supported on a transparent plate or impaled on a pin. The sample is treated systemically or post-surgically with a fluorescence dye having binding affinity to diseased cells. That is, systemic application (prior to or during surgery) of a dye to stain diseased cells in vivo and/or post-surgery application of a dye to resection tissue cells can be performed. At each angle, the sample is illuminated by a white light for normal pictures and then illuminated with fluorescence-causing, diffused laser light for causing the sample to fluoresce. The white-light pictures are used to create a three-dimensional (3-D) model of the sample in a computer, and the fluorescence pictures are used to paint the model so that diseased portions are shown. A surgeon can then view the 3-D model, rotating it and zooming, so that he or she can determine if she cut enough margin around the tumor so that none is left in the patient.

The sample can be moved with precision stepper motors, etc. so that registration in space of features on the sample from the 2-D pixels is more robust. The entire system can be hosted in an operating room, and a conveyor system can help move multiple main and peripheral samples into the camera's and lights' imaging volume in quick succession.

Some embodiments of the invention are related to an apparatus for imaging a biological sample with fluorescence. The apparatus includes an imaging stage having a transparent portion for holding at least a portion of a biological sample within an imaging volume, a first rotary bearing having a first rotational axis configured to project through the imaging volume, a leg extending between the stage and the first rotary bearing, the leg offsetting the stage from the first rotary bearing, a second rotary bearing having a second rotational axis configured to project through the imaging volume, the second rotational axis being orthogonal to the first rotational axis, an armature extending between the first and second rotary bearings, a visible light source configured to illuminate the imaging volume, a fluorescence excitation light source configured to illuminate the imaging volume, and a camera configured to have a depth of focus within the imaging volume.

The apparatus can include a computer processor operatively connected with a machine-readable non-transitory medium embodying information indicative of instructions for causing the computer processor to perform operations including taking reflected light images of a biological sample on the stage using the camera while the visible light source is illuminated, rotating the stage around angles of the first or second rotational axis between taking the reflected light images, at least one image of the reflected light images taken of the sample through the transparent portion of the stage, collecting fluorescence images of the biological sample using the camera while the fluorescence excitation light source is illuminated, turning the stage around the angles of the first or second rotational axis between the fluorescence images, at least one image of the fluorescence images collected of the sample through the transparent portion of the stage, and rendering an image produced from the reflected light images and the fluorescence images.

The apparatus can further include constructing a reflected light three-dimensional (3-D) model of the sample using the reflected light images and adding fluorescence information to the 3-D model using the fluorescence images, wherein the rendered image is rendered from the 3-D model.

Some embodiments are related to an apparatus for imaging a biological sample with fluorescence. The apparatus includes an imaging stage having a transparent portion for holding at least a portion of a biological sample within an imaging volume, a rotary bearing having a first rotational axis configured to project through the imaging volume, a leg extending between the stage and the rotary bearing, the leg offsetting the stage from the rotary bearing, a plurality of telescoping arms, each arm have a compressed position and an extended position, the arms connected by pivot points to the rotary bearing, wherein a differential extension of at least one telescoping arm from at least one other telescoping arm is configured to tilt the stage with respect to a second rotational axis, the second rotational axis being orthogonal to the first rotational axis, a visible light source configured to illuminate the imaging volume, a fluorescence excitation light source configured to illuminate the imaging volume, and a camera configured to have a depth of focus within the imaging volume.

The apparatus can include constructing a reflected light three-dimensional (3-D) model of the sample using the reflected light images, and adding fluorescence information to the 3-D model using the fluorescence images, wherein the rendered image is rendered from the collocated 3-D model.

The apparatus can include actuators selected from the group consisting of a direct current (DC) motor, a linear stepper, a linear motor, a piston, and a hydraulic arm, wherein the extendible arms are connected with the actuators.

In some embodiments, the present invention provides a method for imaging a biological sample from a subject, the method comprising:
 i) illuminating the biological sample on an imaging stage with visible light and using a camera to generate a plurality of 2-D first images;
 ii) illuminating the biological sample on the imaging stage with near infrared light and using the camera to generate a plurality of 2-D second images;
 iii) constructing a first 3-D model of the biological sample based upon the plurality of 2-D first images; and
 iv) adding fluorescence information to the 3-D model of the biological sample based upon the plurality of 2-D second images.

In the method the 3-D model can be labeled a first 3-D model, and the method further includes constructing a second 3-D model of the biological sample based upon the plurality of 2-D second images, and projecting the second 3-D model onto the first 3-D model by interposing points of the second 3-D model into the first 3-D model to add fluorescence information to the 3-D model.

Some embodiments are related to a method for imaging a biological sample from a subject. The method includes taking reflected light 2-D images of a biological sample at a plurality of angles using a camera, applying a probe biomolecule having a binding affinity to a subset of cells of the biological sample, the biomolecule connected with a fluorescent dye marker, illuminating the biological sample with a fluorescence excitation light source having one or more frequencies configured to cause the fluorescent dye marker to fluoresce at one or more frequencies different than those of the fluorescence excitation light source, collecting fluorescence 2-D images of the biological sample at a plurality of angles using a camera during the illuminating, constructing a first 3-D model of the biological sample based upon the reflected light 2-D images, adding fluorescence information based upon the fluorescence 2-D images to the 3-D model, and rendering an image produced from the 3-D model.

These and other aspects, objects and embodiments will become more apparent when read with the detailed description and figures which follow.

The figures will be used below to illustrate different embodiments in accordance with the invention. The figures are specific examples of embodiments and should not be interpreted as limiting embodiments, but rather exemplary forms and procedures.

DETAILED DESCRIPTION

I. Definitions

The term "subject," "patient," or "individual" typically refers to humans, but also to other animals including, e.g., other primates, rodents, canines, felines, equines, ovines, porcines, and the like.

An "imaging volume" or imaging window is formed by the illumination light field(s), imaging depth-of-focus of an object lens, and field of view of the imaging head, or as otherwise known in the art.

A "rotor bearing" includes a hub, axle, or other mechanical element that bears contact between at least two parts that allows for rotation around an axis, or as otherwise known in the art. A rotary bearing may include circular tracks and cages for ball bearings, lubricant surfaces, and other friction-reducing implements.

II. Embodiments

Figure 1:
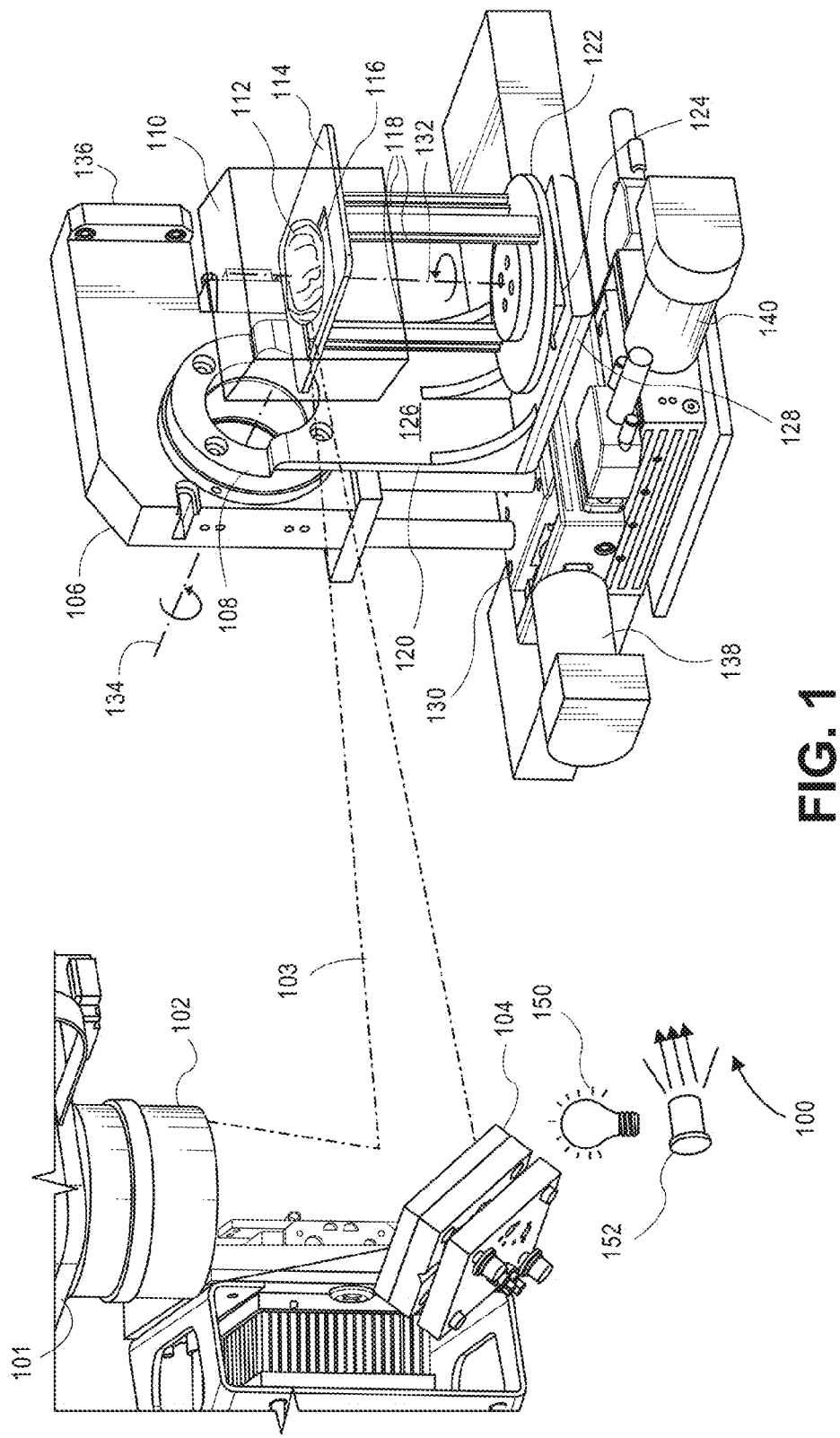
FIG. 1 illustrates a two-rotational bearing apparatus in accordance with an embodiment.

FIG. 1 illustrates a dual-rotational bearing apparatus in accordance with an embodiment. In imaging system 100, camera 101 has objective lens 102. For space considerations, its view is reflected off of mirror 104. Camera focus lines 103 are shown to focus within imaging volume 110.

One or more white lights 150 illuminate imaging volume 110. Fluorescence excitation laser 152 provides fluorescence excitation light to imaging volume 110 as well. These illumination sources are used to illuminate sample 112.

Illumination sources may be mounted proximate to the sample in order to illuminate the sample with white light, monochrome light, near-infrared (IR) or other fluorescence lighting, and/or other electromagnetic radiation.

Sample handling apparatus 106 includes rotary bearing 108 having horizontal axis 134. Rotary bearing 108 is attached to a motor mounted at interface 136 so that the motor controls the movement and precise position of the rotary portion of the bearing. Horizontal axis 134 is aligned to pass through imaging volume 110. L-shaped armature 120 extends from vertical element 126, which attaches to rotary bearing 108, to horizontal element 128. Horizontal element 128 supports another rotary bearing, rotary bearing 124. Rotary bearing 124 moves bottom portion 122 of platform 114 around axis 132 with a low-profile stepper motor, which is configured to propel the stage in precise increments to different angles. Rotary bearing 124 allows the stage—and the sample—to be rotated 360° degrees. As rotary bearing 124 is supported by movable armature 120, its axis 132 can go from vertical to tilted orientations.

Platform 114 comprises bottom portion 122, three legs 118, and imaging stage 114. The three legs offset or hold the sample away from the bottom rotary bearing so that there is less viewing obstruction from the bottom. Transparent portion 116 of imaging stage 114 can be a through hole (with nothing in it) or a transparent glass slide, as shown. This holds sample 112 within imaging volume 110.

The sample handling apparatus includes translation bearing 130, an 'x-y table' that can move the imaging stage in or out of the imaging volume. Linear translational motors 138 and 140 move translation bearing 130 in horizontal directions in precise increments. This can help in focusing when large samples are imaged. The linear motion table can also move samples in or out of the imaging volume to an area where there is more space for accessibility. For example, a sample may be placed on the imaging stage and then moved to a position inside a light-tight housing where the imaging volume is.

Figure 2:
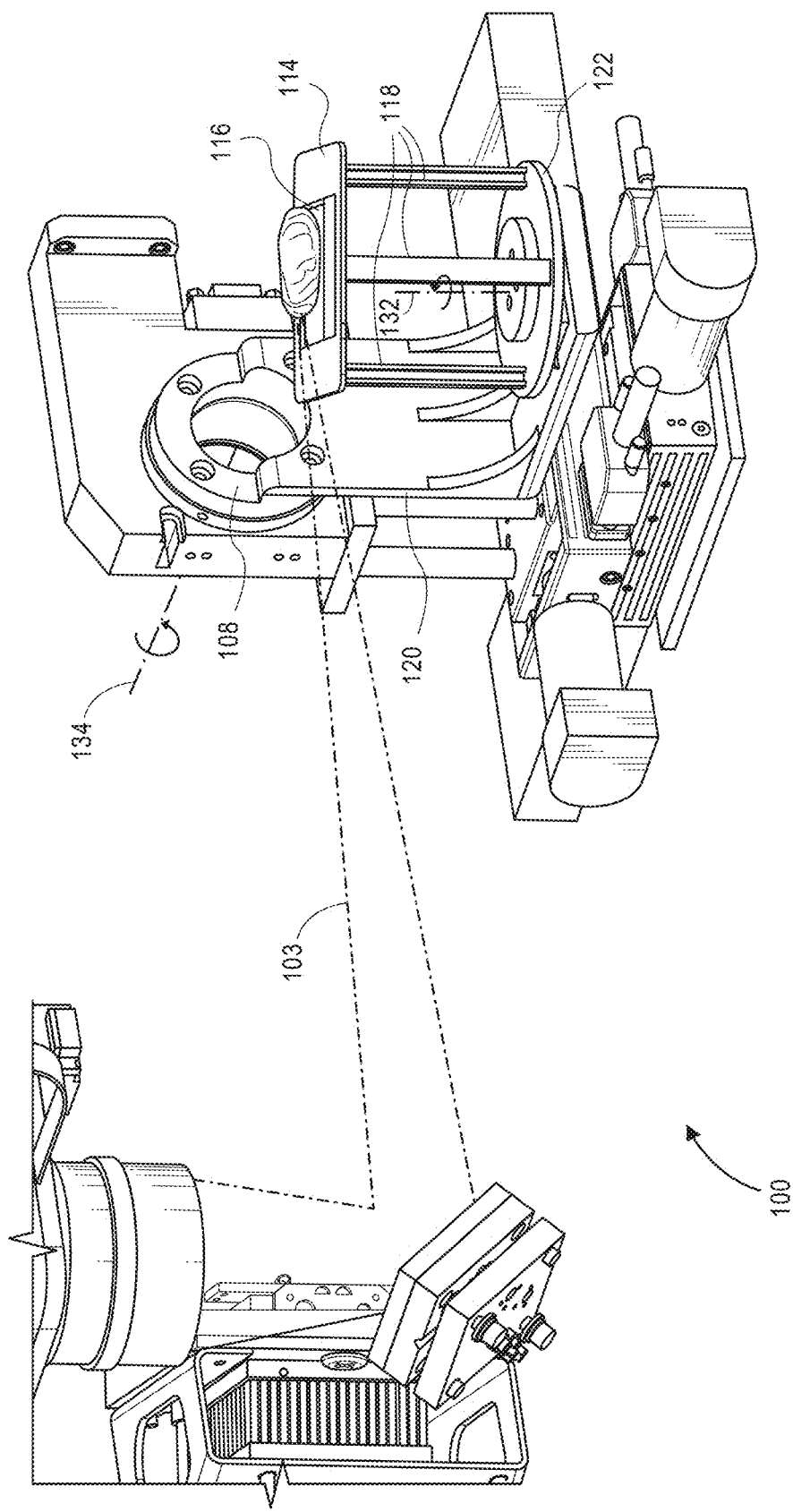
FIG. 2 illustrates the apparatus of FIG. 1 rotated through a vertical axis.

FIG. 2 illustrates the apparatus of FIG. 1 rotated through a vertical axis using the motor. In system 100, camera focus lines 103 show that the camera is focused within the imaging volume. Rotary bearing 108 has not been rotated through axis 134, and so armature 120 is in the same position. The sample has been rotated around axis 132 by rotating the imaging platform, comprising bottom section 122, legs 118, and imaging stage 114. Transparent portion 116 continues to hold the sample.

Figure 3:
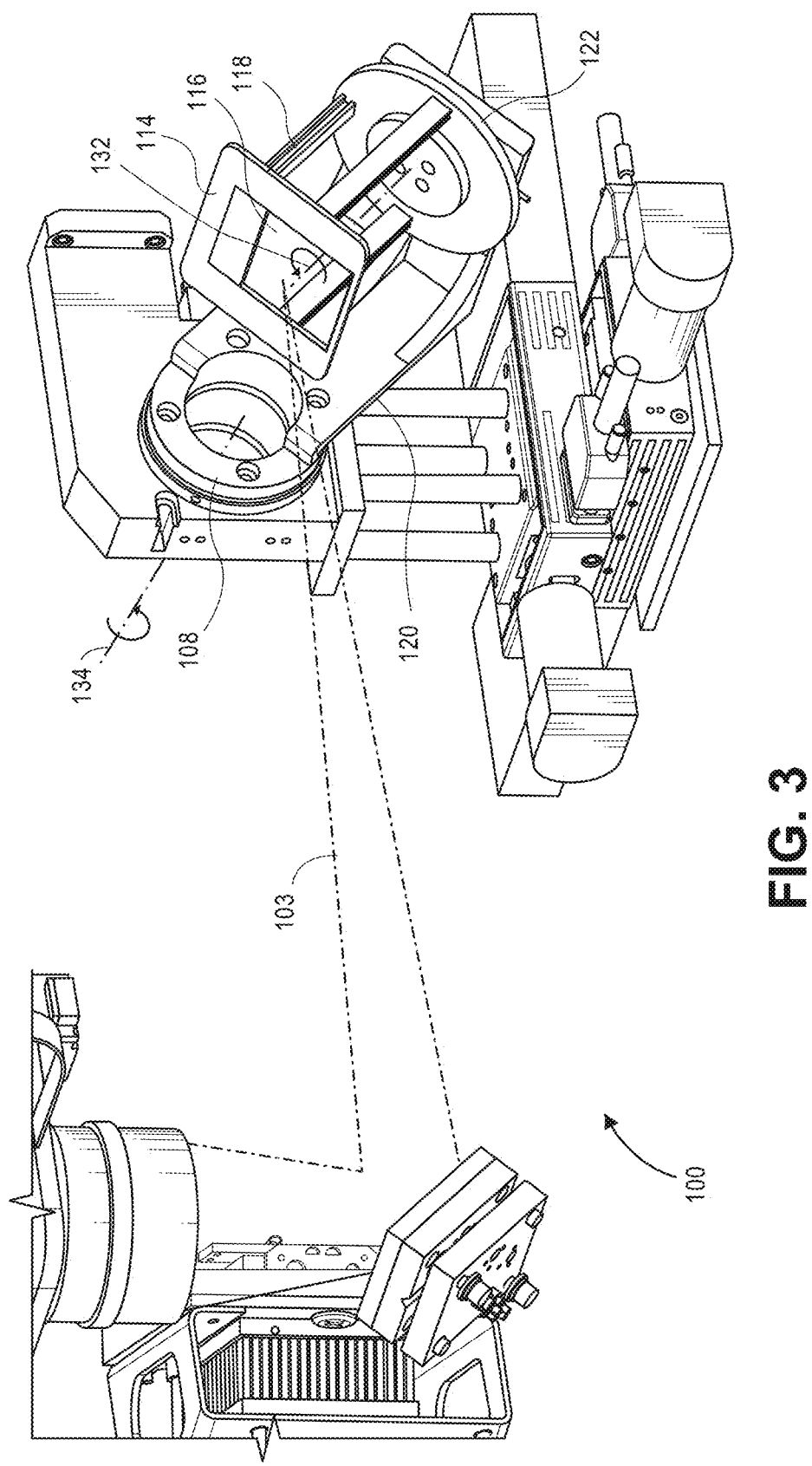
FIG. 3 illustrates the apparatus of FIG. 1 rotated through a horizontal axis.

FIG. 3 illustrates the apparatus of FIG. 1 rotated through a horizontal axis. L-bracket 120 now holds the bottom portion 122 of the stage (and legs 118, imaging stage 114, and transparent portion 116) in a tilted manner, such that bottom rotary bearing's rotational axis 132 is no longer vertical. However, bottom rotary bearing's rotational axis 132 is still perpendicular to the side rotary bearing's axis 134.

In the tilted position shown, the sample can be rotated using the bottom bearing so that oblique top angles of the sample can be imaged by the camera. The maximum tilt of the side rotary bearing may be limited to 30°-45° in order to lessen the chance of a sample sliding or tumbling off of the glass.

In some embodiments in which there is no glass but instead one or more pins upon which a sample is impaled in order to hold it into position, there may be no limit to the maximum tilt.

Figure 4:
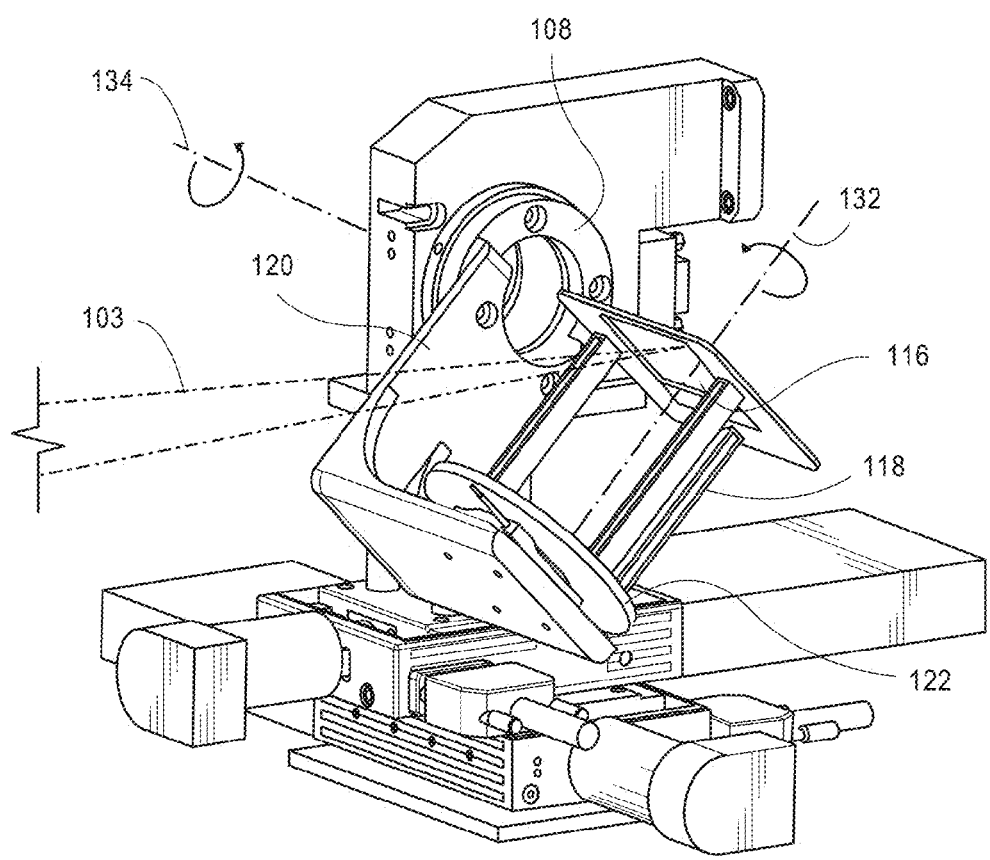
FIG. 4 illustrates the apparatus of FIG. 1 rotated through a horizontal axis such that a sample can be viewed through a transparent portion of an imaging stage.

FIG. 4 illustrates the apparatus of FIG. 1 rotated through rotary bearing 108 horizontal axis 134 such that a sample can be viewed through transparent portion 116 of the imaging stage. In this respect, an underside of the sample can be imaged by the camera through focal lines 103 and illuminated by the white light and laser. As legs 118 and armature 120 offset the rotating bottom 122 of imaging stage so that it does not occlude the transparent 116 bottom of the imaging stage, the camera may peer through transparent portion 116 and take images while the bottom rotary bearing is rotated through different angles.

Figure 5:
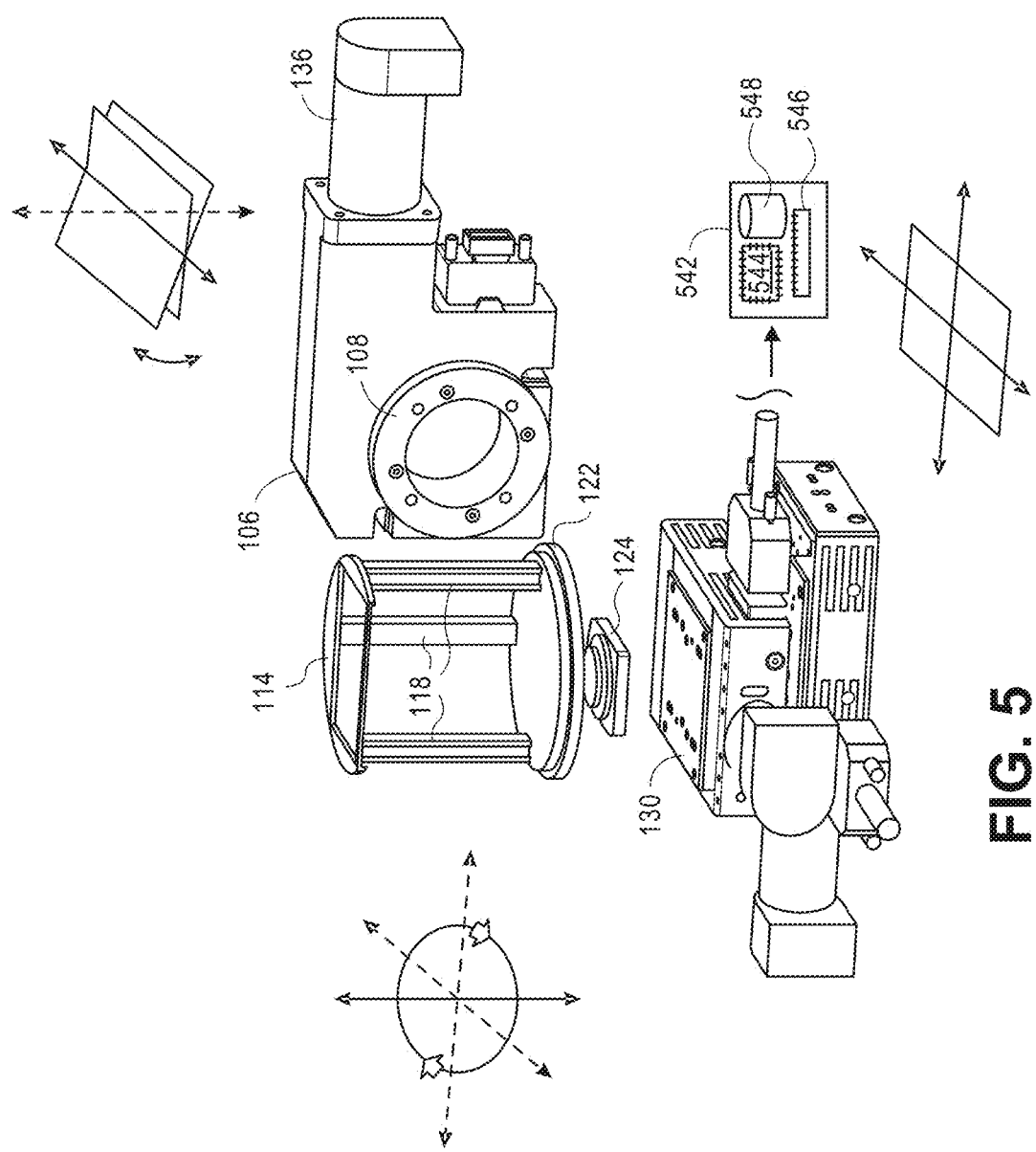
FIG. 5 illustrates an exploded view of the apparatus of FIG. 1.

FIG. 5 illustrates an exploded view of the apparatus of FIG. 1. The sample holder, which includes bottom portion 122, legs 118, and imaging stage 114, is rotated by a rotation stage, rotary bearing 124, around the Rz axis as shown. Sample handling mechanism 106 includes rotary bearing 108, which is driven by motor 136 for tilting the imaging stage with respect to the Rx and/or Ry axes as shown. Two-axis translational stage 130 can be used to translate in the x or y directions.

Computer 542, which includes microprocessor 544, memory 546, and nonvolatile storage 548, controls the motors for exact positioning of the stage. Computer 542 received 2-D images from the camera, both white light and fluorescence images, and processes them to create a 3-D model of the sample 'painted' with fluorescence portions.

Figure 6:
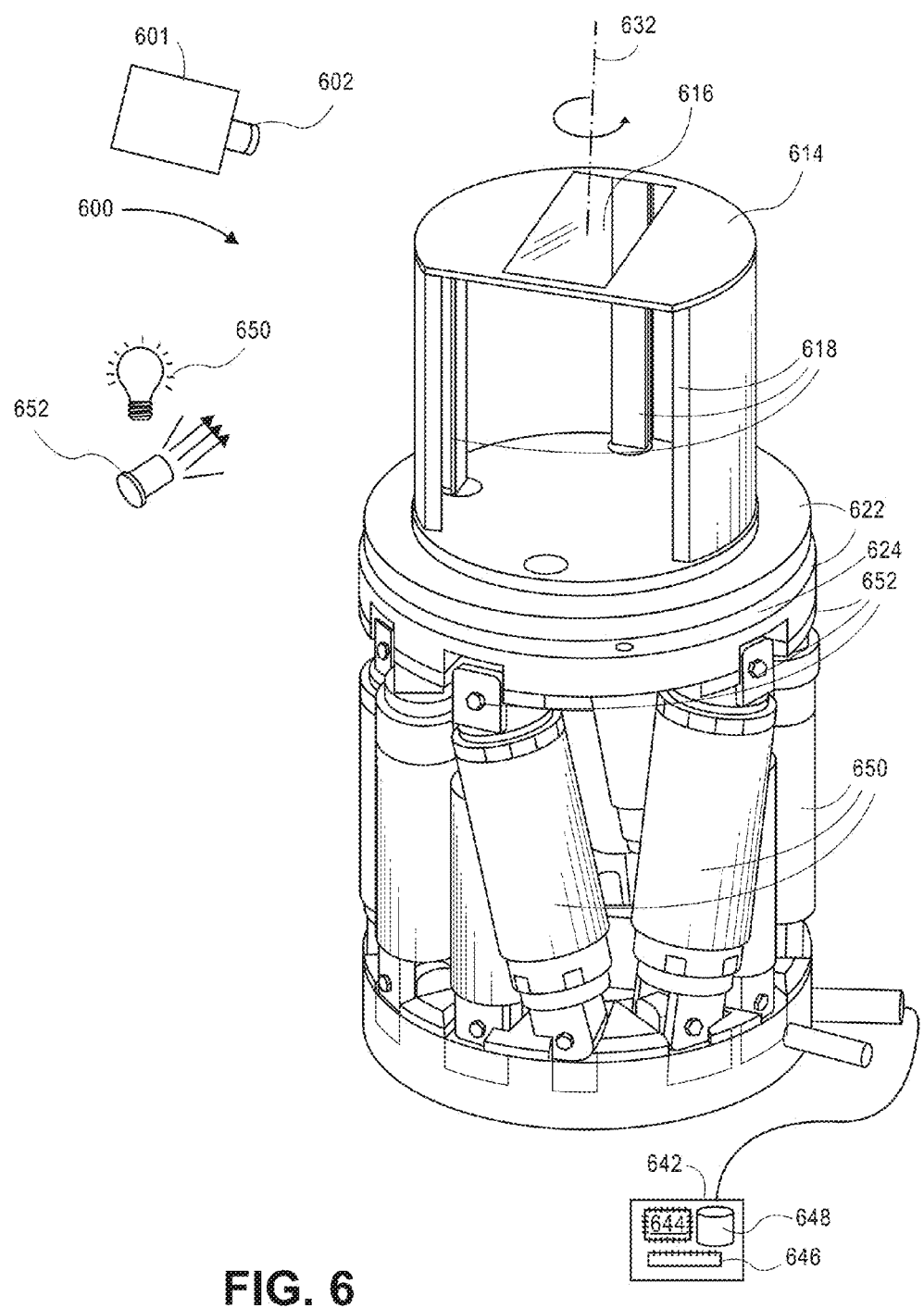
FIG. 6 illustrates an alternate imaging stage support mechanism in accordance with an embodiment.

FIG. 6 illustrates an alternate imaging stage support mechanism in accordance with an embodiment. In system 600, at the top of the sample stage is a rectangular slide area 616 upon which a sample can be rested. Other slide shapes, sizes, and curvatures can be used. Legs 618 support imaging stage 614, which surrounds rectangular slide area. The bottom of the sample holder is affixed to low-profile rotary bearing 622 moved by motor 624, which can be moved in small, precise increments with a motor.

Extendible, telescoping piston arms 650, eight in total, each with a separate pivot point 652 on the bottom of the rotary bearing 622, can be differentially extended or compressed in order to tilt the sample. The piston arms are offset in angles with respect to one another such that a differential extension results in a tilting of the imaging stage.

Computer 642, which includes processor 644, memory 646, and non-volatile, hard disk memory 648, control movement of the stage. Computer 642 also controls camera 601, with objective lens 602, and illumination sources 650 (mono-chrome light) and 652 (diffused laser).

Figure 7:
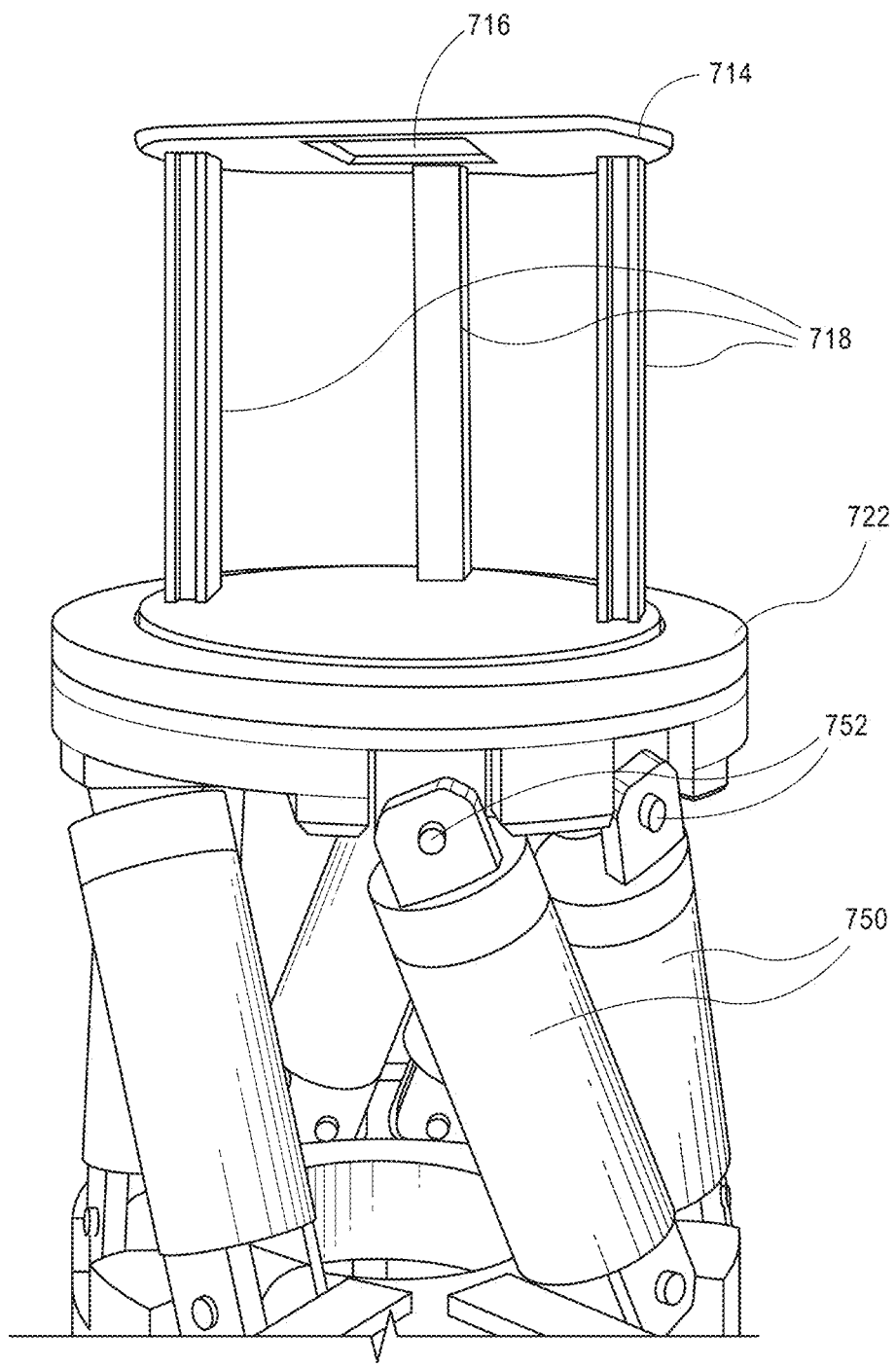
FIG. 7 illustrates an alternate imaging stage support mechanism in accordance with an embodiment.

FIG. 7 illustrates an alternate imaging stage support mechanism in accordance with an embodiment. Six telescoping piston arms 750, all aligned in a common direction, support the sample stage. They are connected to bottom of rotary bearing 722 by mechanical pins joints 752 at different positions and orientations on rotary bearing 722. Rotary bearing 722 supports legs 718, which in turn support imaging stage 714 and transparent portion 716.

Figure 8:
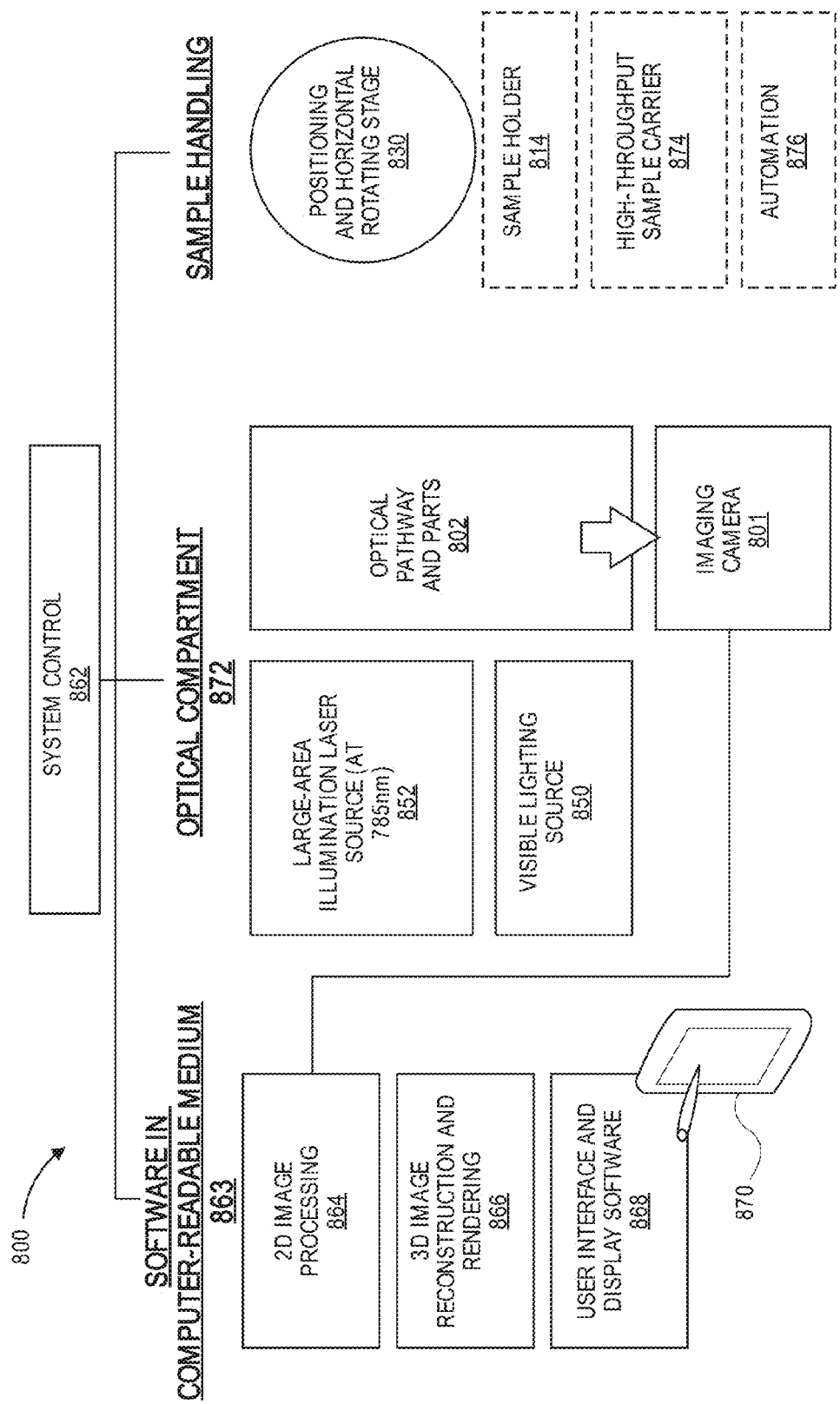
FIG. 8 is block diagram of a system in accordance with an embodiment.

FIG. 8 is block diagram of a system in accordance with an embodiment. In system 800, system control 862 provides control to software in computer-readable medium 863 for 2D image processing 864, 3D image reconstruction and rendering 866, and a user interface and display 686 modules. The software may also display to user device 870 and control imaging camera 801.

System control 862 also provides inputs to optical compartment 872. Optical compartment 872 includes large-area illumination laser source 852 (at 685 nanometers (nm) or 785 nm), a visible lighting source 850, and an optical pathway and parts 802. This may include imaging camera 801.

System control 862 provides inputs to sample handing modules. Sample handling is provided for positioning and otherwise handing one or more samples. Sample handling can include a positioning and horizontal rotating stage 830, a curved or flat sample holder 814, a high-throughput sample carrier 874, and automation conveyor mechanisms 876.

Figure 9:
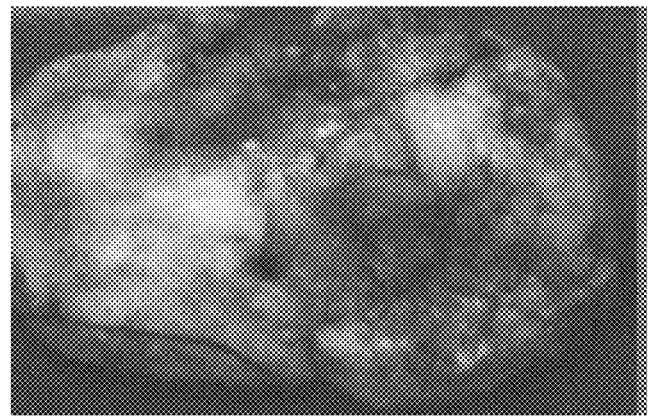
FIG. 9 is a reflected light 2-D image of a biological sample in accordance with an embodiment.
Figure 10:
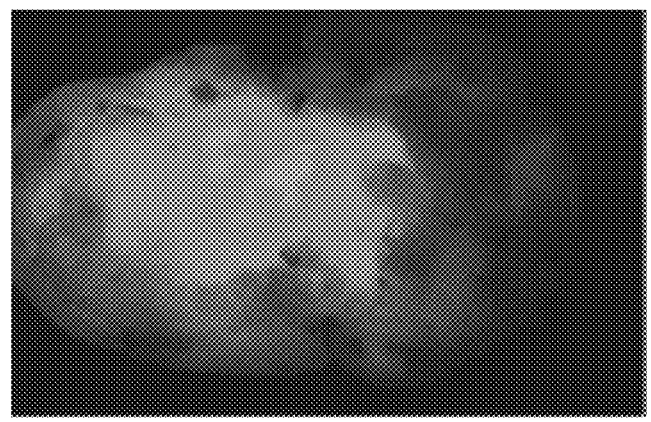
FIG. 10 is a fluorescence 2-D image of the biological sample in FIG. 9 in accordance with an embodiment.

FIG. 9 is a reflected light 2-D image of a biological sample, and FIG. 10 is a fluorescence 2-D image of the biological sample in FIG. 9 in accordance with an embodiment. The reflected light image shows a view of an excised biopsy tissue sample when illuminated with a bright white light. Ambient light can also be used, or a single color illumination light can also be used. The fluorescence image is taken after a probe biomolecule with a binding affinity for tumor cells is applied to the tumor. This can occur in vivo or ex vivo. The probe molecule is connected with a fluorescent dye marker directly or with a second probe molecule. When the sample is illuminated with a frequency of light meant to cause fluorescence of the fluorescent dye, the camera (which may be cooled) is used to pick up the faint image of the fluorescence. There may be a light-tight housing around the sample in order to shut out ambient light for these images.

The fluorescence image was acquired in a dark environment, as such fluorescence is quite dim. A light tight housing surrounding the camera and sample handling apparatus can help seal out light in a bright operating room. A door with a light-tight seal may be used to access the sample area.

The camera has an actively cooled heat exchanger that keeps the charge coupled device (CCD) imaging sensor of the camera at low temperatures. The cooling can prevent optical background and camera noise (e.g., dark, blooming, and radiation events). The camera, optics, and other elements used in the exemplary embodiment are described in U.S. Pat. Nos. 7,286,232, 8,220,415, and 8,851,017.

Figure 11A:
FIG. 11A is a picture of the skin of a patient with a tumor in accordance with an embodiment.
Figure 11B:
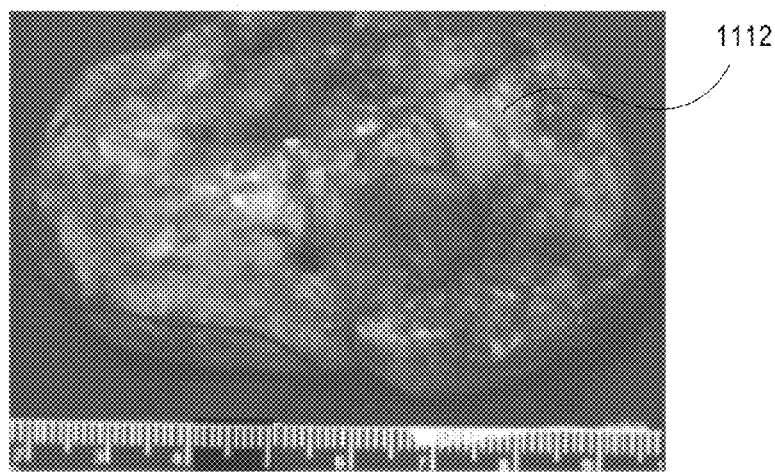
FIG. 11B is a white-light image of an extracted tumor in accordance with an embodiment.
Figure 11C:
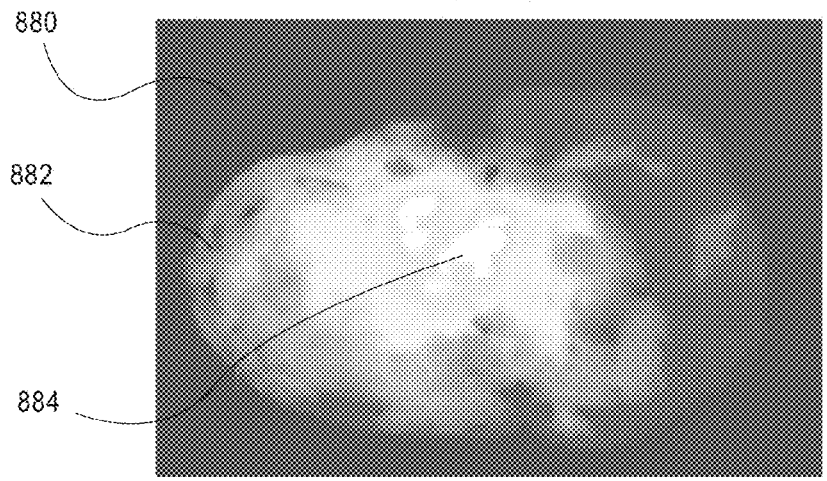
FIG. 11C is a rendered image of a sample in accordance with an embodiment.

FIGS. 11A-11C include images of a patient's tumor, biological sample, and rendered image of the sample in accordance with embodiments. In FIG. 11A, the skin above a tumor is shown in a subject. Markings on the skin of the subject are used for surgery planning. In FIG. 11B, a true color image of an excised tumor is shown. FIG. 11C shows a rendering from a 3-D model of the tumor. The 3-D model can be used to determine if appropriate margins have been applied around the tumor tissue.

In certain aspects, the present invention provides methods to assist gross examination to improve time efficiency and pathological accuracy of histological examinations. The methods herein described significantly improve the surgical outcome and reduce the local recurrences of cancers. In certain aspects, the present invention provides a fluorescence imaging system to provide 3-D surface mapping of a fluorescence image on a reconstructed image model of a surgical specimen to localize the signal representing disease tissue on the specimen. In certain aspects, the devices and methods described herein assist gross examination prior to sectioning for histological analysis.

In one embodiment, the present invention provides a method for imaging a biological sample from a subject, the method comprising:
 i) illuminating the biological sample on an imaging stage with visible light and using a camera to generate a plurality of 2-D first images;
 ii) illuminating the biological sample on the imaging stage with near infrared light and using the camera to generate a plurality of 2-D second images;
 iii) constructing a first 3-D model of the biological sample based upon the plurality of 2-D first images; and
 iv) adding fluorescence information to the 3-D model of the biological sample based upon the plurality of 2-D second images.

In certain aspects, the method provides illuminating a biological sample with visible light and capturing a plurality of first 2-D images using visible light. The method further includes illuminating the same or different biological sample with near infrared light and using the camera to capture a plurality of second 2-D images using infrared light. Preferably a single sample is used, so that both illumination techniques can be used concurrently on a single sample, without the visible light images changing the appearance of the near infrared images or vice versa.

Fluorophore methods utilize molecules that absorb light of one spectrum and emit light of a different spectrum. To utilize a visible image in combination with a fluorophore (e.g., an infrared or near-infrared fluorophore), care should be taken to ensure that the spectra of light variously absorbed, reflected, and emitted do not significantly overlap to confound differentiation of the components from each other and differentiation of the components from endogenous tissue material. Provided herein are methods utilizing a combination of invisible light (e.g., infrared or near-infrared) fluorophores and visible light images to visualize and analyze biological samples.

In certain aspects, the plurality of 2-D first images are taken at different angles of the imaging stage rotated through a vertical axis. In certain other aspects, the plurality of 2-D first images are taken at different angles of the imaging stage rotated through a horizontal axis.

In certain aspects, the plurality of 2-D second images are taken at different angles of the imaging stage rotated through a vertical axis. In certain aspects, the plurality of 2-D second images are taken at different angles of the imaging stage rotated through a horizontal axis.

In certain preferred aspects, the imaging stage is transparent.

In certain aspects, the illumination of the biological sample with visible light is performed at one or more wavelengths of about 380 nm to about 700 nm. These wavelengths include, for example, about 380, 390, 400, 425, 450, 475, 500, 525, 550, 575, 600, 625, 650, 675, or about 700 nm. These can occur in combination, such as in broadband white light.

In certain aspects, the illumination of the biological sample of near infrared light is performed at one or more wavelengths of about 650 nm to about 1400 nm. These wavelengths include, for example, about 700, 725, 750, 775, 800, 825, 850, 875, 900, 910, 920, 930, 940, 950, 960, 970, 980, 990, 1000, 1100, 1200, 1300, and 1400 nm. Sometimes these wavelengths are referred to as being in the NIR-I (between 750 and 1060 nm) and NIR-II (between 1000 nm and 1700 nm) wavelength regions.

In certain aspects, the biological sample comprises a fluorescent dye. In one aspect, the fluorescent group is a near-infrared (NIR) fluorophore that emits in the range of between about 650 to about 1400 nm. Use of near infrared fluorescence technology is advantageous in the methods herein as it substantially eliminates or reduces background from auto fluorescence of tissue. Another benefit to the near-IR fluorescent technology is that the scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 990 nm) or NIR-II region (between about 1000 nm and 1400) in biological tissue makes NIR fluorescence a valuable technology for imaging and subcellular detection applications that require the transmission of light through biological components.

In certain aspects, the fluorescent group is preferably selected form the group consisting of IRDye® 800RS, IRDye® 800CW, IRDye® 800, Alexa Fluor® 660, Alexa Fluor®680, Alexa Fluor® 700, Alexa Fluor® 750, Alexa Fluor® 790, Cy5, Cy5.5, Cy7, DY 676, DY680, DY682, and DY780. In certain aspects, the near infrared group is IRDye® 800CW, IRDye® 800, IRDye® 700DX, IRDye® 700, or Dynomic DY676.

In certain aspects, the fluorescent dye is contacted with the biological sample prior to excising the biological sample from the subject. For example, the dye can be injected or administered to the subject prior to surgery or after surgery. In certain aspects, the dye is conjugated to an antibody, ligand, or targeting moiety having an affinity to a tumor or recognizes a tumor antigen. In certain aspects, the fluorescent dye comprises a targeting moiety. IN one aspect, the surgeon "paints" the tumor with the dye.

In some aspects, the targeting molecule is an antibody that binds an antigen such as a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, or an osteosarcoma cell surface antigen.

In certain aspects, the methods described herein are used in various oncology surgical procedures. For example, labeling can be achieved by using NIR fluorescence dyes for the of an excellent signal-to-background ratio and minimized scattering and absorption effects. Suitable example are a NIR label such as ICG, which pools in hyperpermeable cancer tissues, or EGFR targeted IRDye® 800CW-panitumumab (or similar moiety).

In certain aspects, the fluorescent dye is contacted with the biological sample after excising the biological sample from the subject. In this manner, dye can contacted to the tissue at the margins. In certain aspects, the biological sample comprises a tumor, such as tumor tissue or cells.

In certain aspects, the first 3-D model comprises both healthy tissue and diseased tissue. The first 3-D model is constructed of the biological sample based upon the plurality of 2-D first images. In certain aspects, the second 3-D model comprises diseased tissue. For example, the second 3-D model is constructed of the biological sample based upon the plurality of second 2-D images. In one aspect, the first 3-D model is made-up of visible images and the second 3-D model is made-up of fluorescent images. In another aspect, the first 3-D model is made-up of fluorescent images and the second 3-D model is made-up of visible images.

In certain aspects, using the methods of the present invention, it is possible to identify a diseased tissue area or cancerous area (e.g., fluorescent 3-D image) within a broader healthy tissue area (e.g., visible 3-D image). In this manner, the precise location of the diseased tissue can be identified.

In certain aspects, the biological sample comprises a peripheral biopsy of a tissue sample previously removed. In another aspect, the biological sample is tumor tissue such as a breast core biopsy. The biological sample size can a tissue slice all the way to a large specimen.

In certain aspects, registration of the biological sample is maintained. For example, if a tumor biopsy is removed from a subject, the exact location of the biopsy is maintained.

In certain aspects, integrity of the biological sample is maintained.

In certain aspects, imaging of the biological sample is performed while the subject is undergoing surgery.

In one aspect, a pathologist determines where to take frozen sections from a whole primary specimen that has been excised from a subject. Typically, the pathologist will communicate margin status to the surgeon. In certain aspects, the surgeon will send the whole primary specimen to the frozen lab and the pathologist will use frozen sections to determine the status of the margins. Using the inventive devices and methods, fluorescence is used to guide margin sampling for histological assessment. In certain instances, the methods herein are performed before sectioning.

In another aspect, a surgeon can send 10-20 margins to the frozen lab that were excised from a subject in situ or the post-resection wound bed. A pathologist typically examines 10-50 micron (pm) sections from each specimen. Slices are typically 10 µm in thickness. On average, this represents less than 1% of the margin. Utilizing the methods described herein, the pathologist images each margin prior to histological sectioning. The fluorescent information is used to guide the sectioning of the margin.

The devices and methods provide image-guide pathology to improve accuracy of frozen section analysis, improve final clear margin rates, improve survival by decrease local recurrence, and reduce operation time by eliminating the need to sample multiple areas within a specimen.

Figure 12:
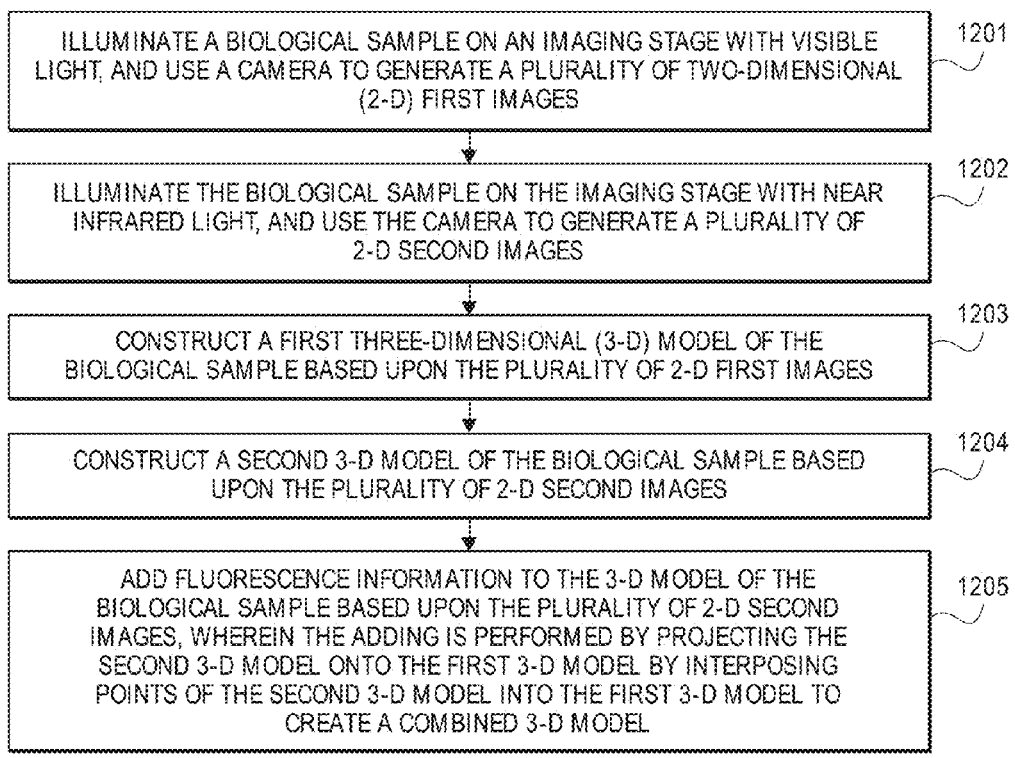
FIG. 12 is a flowchart illustrating an embodiment in accordance with the present invention.

FIG. 12 is a flowchart of a process in accordance with an embodiment. In operation 1201, a biological sample on an imaging stage is illuminated with visible light, and a camera is sued to generate a plurality of two-dimensional (2-D) first images. In operation 1202, the biological sample on the imaging stage is illuminated with near-infrared light, and the camera is used to generate a plurality of 2-D second images. In operation 1203, a first three-dimensional (3-D) model of the biological sample is constructed based upon the plurality of 2-D first images. In operation 1204, a second 3-D model of the biological sample is constructed based upon the plurality of 2-D second images. In operation 1205, fluorescence information is added to the 3-D model of the biological sample based upon the plurality of 2-D second images. The adding is performed by projecting the second 3-D model onto the first 3-D model by interposing points of the second 3-D model into the first 3-D model to create a combined 3-D model.

Figure 13:
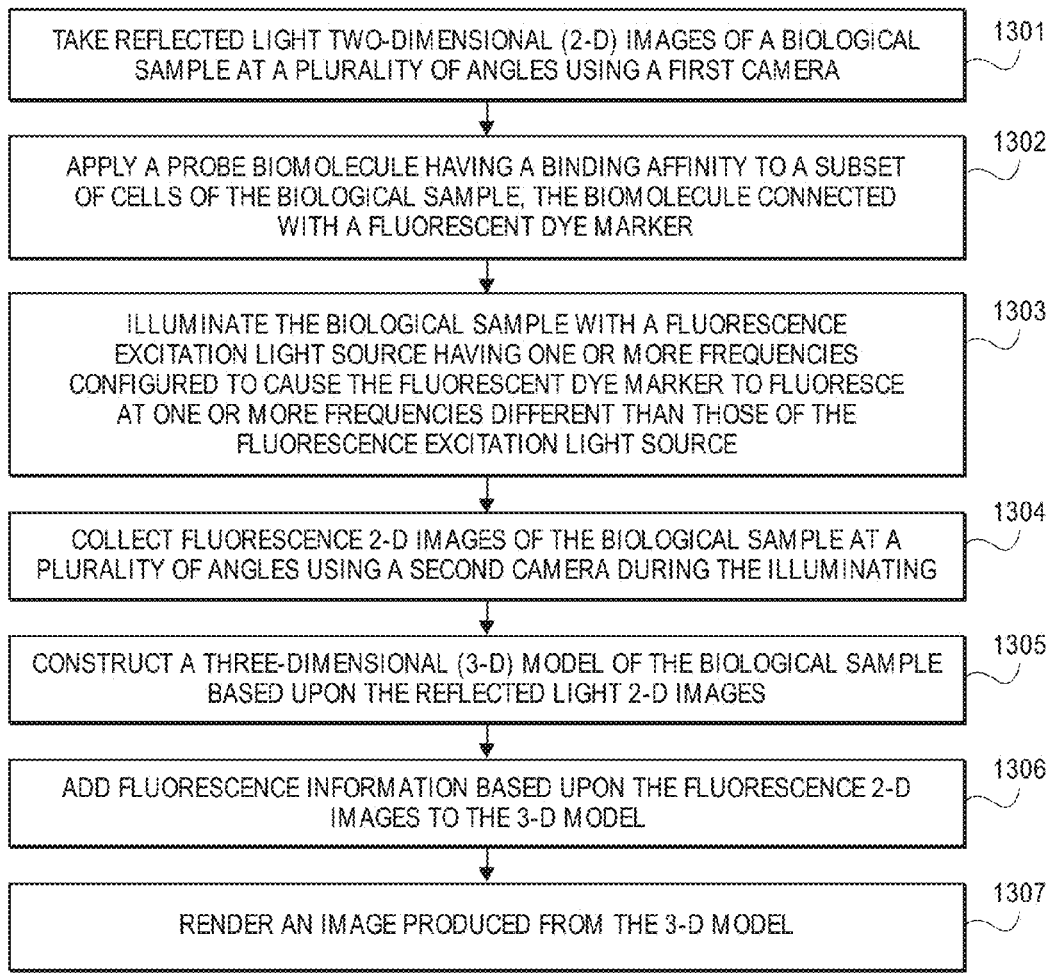
FIG. 13 is a flowchart illustrating an embodiment in accordance with the present invention.

FIG. 13 is a flowchart of a process in accordance with an embodiment. In operation 1301, reflected light two-dimensional (2-D) images are taken of a biological sample at a plurality of angles using a camera. In operation 1302, a probe biomolecule having a binding affinity to a subset of cells of the biological sample is applied to the biological sample, the biomolecule connected with a fluorescent dye marker. In operation 1303, the biological sample is illuminated with a fluorescence excitation light source having one or more frequencies configured to cause the fluorescent dye marker to fluoresce at one or more frequencies different than those of the fluorescence excitation light source. In operation 1304, fluorescence 2-D images of the biological sample are collected during the illuminating at a plurality of angles using a camera. In operation 1305, a three-dimensional (3-D) model of the biological sample is constructed based upon the reflected light 2-D images. In operation 1306, fluorescence information based upon the fluorescence images is added to the 3-D model. In operation 1307, an image produced from the 3-D model is rendered.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An apparatus for imaging a biological sample with fluorescence, the apparatus comprising:

an imaging stage having a transparent portion for holding at least a portion of a biological sample within an imaging volume;

a first rotary bearing having a first rotational axis configured to project through the imaging volume;

a leg extending between the stage and the first rotary bearing, the leg offsetting the stage from the first rotary bearing;

a second rotary bearing having a second rotational axis configured to project through the imaging volume, the second rotational axis being orthogonal to the first rotational axis;

an armature extending between the first and second rotary bearings;

a visible light source configured to illuminate the imaging volume;

a fluorescence excitation light source configured to illuminate the imaging volume; and a camera configured to have a depth of focus within the imaging volume.

2. The apparatus of claim 1 further comprising:
a computer processor operatively connected with a machine-readable non-transitory medium embodying information indicative of instructions for causing the computer processor to perform operations comprising:
taking reflected light images of a biological sample on the stage using the camera while the visible light source is illuminated;
rotating the stage around angles of the first or second rotational axis between taking the reflected light images, at least one image of the reflected light images taken of the sample through the transparent portion of the stage;
collecting fluorescence images of the biological sample using the camera while the fluorescence excitation light source is illuminated;
turning the stage around the angles of the first or second rotational axis between the fluorescence images, at least one image of the fluorescence images collected of the sample through the transparent portion of the stage; and
rendering an image produced from the reflected light images and the fluorescence images.

3. The apparatus of claim 2 wherein the operations further comprise:
constructing a reflected light three-dimensional (3-D) model of the sample using the reflected light images; and
adding fluorescence information to the 3-D model using the fluorescence images, wherein the rendered image is rendered from the 3-D model.

4. The apparatus of claim 3 wherein the constructing of the 3-D model from reflected light images includes silhouette modeling.

5. The apparatus of claim 3 further comprising:
a frame section adjacent to the transparent portion, wherein the constructing of the reflected light 3-D model includes using the frame section for image registration.

6. The apparatus of claim 2 further comprising:
overlaying a reflected light image taken at each angle with a fluorescence image collected at the same angle to render the rendered image.

7. The apparatus of claim 6 wherein the operations further comprise normalizing a contrast of the reflected light images with a contrast of the fluorescence images such that the contrasts are relatively equal.

8. The apparatus of claim 2 wherein at each angle a reflected light image is taken and a fluorescence image is collected before rotating and turning the stage to another angle.

9. The apparatus of claim 1 wherein the leg extends perpendicularly from a flat surface of the transparent portion to the first rotary bearing.

10. The apparatus of claim 9 wherein the leg extends underneath the stage downward toward the first rotary bearing.

11. The apparatus of claim 1 wherein the leg extends parallel with a flat surface of the transparent portion to the first rotary bearing.

12. The apparatus of claim 1 wherein the entire imaging stage is transparent.

13. The apparatus of claim 1 further comprising at least one translational bearing supporting the second rotary bearing, the translational bearing configured to move the stage horizontally in at least one direction.

14. The apparatus of claim 13 wherein the translational bearing is configured to move the stage into and out of the imaging volume.

15. The apparatus of claim 1 further comprising:
a conveyor system for moving a biological sample onto or off of the stage.

16. An apparatus for imaging a biological sample with fluorescence, the apparatus comprising:
an imaging stage having a transparent portion for holding at least a portion of a biological sample within an imaging volume;
a rotary bearing having a first rotational axis configured to project through the imaging volume;
a leg extending between the stage and the rotary bearing, the leg offsetting the stage from the rotary bearing;
a plurality of extendible arms, each arm have a compressed position and an extended position, the arms connected by pivot points to the rotary bearing, wherein a differential extension of at least one extendible arm from at least one other extendible arm is configured to tilt the stage with respect to a second rotational axis, the second rotational axis being orthogonal to the first rotational axis;
a visible light source configured to illuminate the imaging volume;
a fluorescence excitation light source configured to illuminate the imaging volume; and
a camera configured to have a depth of focus within the imaging volume.

17. The apparatus of claim 16 further comprising:
a computer processor operatively connected with a machine-readable non-transitory medium embodying information indicative of instructions for causing the computer processor to perform operations comprising:
taking reflected light images of a biological sample on the stage using the camera while the visible light source is illuminated;
rotating the stage around angles of the first or second rotational axis between taking the reflected light images, at least one image of the reflected light images taken of the sample through the transparent portion of the stage;
collecting fluorescence images of the biological sample using the camera while the fluorescence excitation light source is illuminated;
turning the stage around the angles of the first or second rotational axis between the fluorescence images, at least one image of the fluorescence images collected of the sample through the transparent portion of the stage; and rendering an image produced from the reflected light images and the fluorescence images.

* * * * *